United States Patent [19]

Sawada et al.

[11] Patent Number: 5,305,072
[45] Date of Patent: Apr. 19, 1994

[54] LASER SCATTERING PARTICLE-SIZE DISTRIBUTION ANALYZER WITH IMPROVED SAMPLE CONTAINER DISCHARGE

[75] Inventors: Yoshiyuki Sawada; Toshiya Itoh, both of Miyanohigashi, Japan

[73] Assignee: Horiba, Ltd., Kyoto, Japan

[21] Appl. No.: 928,988

[22] Filed: Aug. 12, 1992

[30] Foreign Application Priority Data

Aug. 17, 1991 [JP] Japan .................. 3-073029

[51] Int. Cl.$^5$ .......... G01N 15/02; G01N 1/10
[52] U.S. Cl. .................. 356/336; 356/246; 356/440; 250/576
[58] Field of Search .................. 356/335–343, 356/244, 246, 410, 414, 416, 440; 250/574, 576, 222.2; 422/63–67, 100, 102, 104

[56] References Cited

U.S. PATENT DOCUMENTS

| | | | |
|---|---|---|---|
| 3,625,485 | 12/1971 | Adler | 356/246 |
| 3,790,760 | 2/1974 | Stiller | 356/335 |
| 4,291,986 | 9/1981 | Satou et al. | 356/440 |
| 4,312,591 | 1/1982 | Tomoff | 356/246 |
| 5,173,741 | 12/1992 | Wakatake | 356/440 |

Primary Examiner—Richard A. Rosenberger
Assistant Examiner—Hoa Q. Pham
Attorney, Agent, or Firm—Price, Gess & Ubell

[57] ABSTRACT

A laser scattering particle-sized distribution analyzer includes a rotary table for movably supporting a plurality of sample cups. A camming mechanism associated with each sample cup holder can be activated to invert a sample cup at a discharge station. Diluting fluid can be sprayed into the inverted cup to ensure a complete discharge of the sample. The sample is then appropriately mixed to ensure the creation of a homogeneous sample with sufficient diluting fluid and delivered to a sample cell for measurement with the laser and detector system.

17 Claims, 5 Drawing Sheets

LASER SCATTERING PARTICLE-SIZE DISTRIBUTION ANALYZER WITH IMPROVED SAMPLE CONTAINER DISCHARGE

BACKGROUND OF THE INVENTION

1. Field of the Invention

The present invention relates to a laser scattering particle-size distribution analyzer comprising an ultrasonic chamber having a sample-circulating pipe connected to a sample cell adjacent a laser measuring station and more particularly to an improved device for inverting a sample container and ensuring a complete discharge of all particles.

2. Description of Related Art

Referring to FIG. 5, a conventional sample-supplying device has samples stored within a plurality of sample cups 52 as shown. A rotary table 51 supports the sample cups 52 and delivers them to a load station wherein a pipette 54 communicately connected with a suction pump 53 sucks up the samples and subsequently delivers them to an ultrasonic chamber 55.

In the above described device, a significant space for moving the pipette 54 up and down and right and left has been required and thus the device has been of a large size due to the space requirement.

In addition, a disadvantage has also occurred in that only a part of the sample within the sample cup 52 is sampled so that measurements can be spoiled, in particular a sample having a large specific gravity and a high viscosity can have components to be measured which will settle on a bottom surface of the sample cup 52 and sediments can be formed in the sample after the lapse of long periods to spoil an accuracy of measurement, whereby obtaining biased data. Thus, the prior art is still seeking an improved sample dispensing apparatus.

SUMMARY OF THE INVENTION

The present invention has been achieved paying attention to the above described matters and it is an object of the present invention to provide a laser scattering particle-size distribution analyzer capable of solving the above described disadvantage by utilizing a portion of a diluent which is also required in a measurement operation.

The laser scattering particle-size distribution analyzer utilizes a sample-supplying device comprising a plurality of cup holders provided on a rotary table for holding a sample cup for a reversely up and down movement, a holder inverting mechanism for reversely turning the cup holders up and down at a discharge position above an ultrasonic chamber and a nozzle for spraying diluent into the inverted sample cups.

An improved laser scattering particle-size distribution analyzer comprises a plurality of sample cups, a rotary table for movably mounting the plurality of sample cups, a cam mechanism for inverting a sample cup to discharge the sample contained therein at a discharge station, a source of diluent fluid, a nozzle system for spraying the diluent fluid into a bottom of the inverted sample cup at the discharge station to ensure a complete discharge of the sample, an ultrasonic chamber for receiving the discharged sample to mix it, a sample cell fluidly connected to the ultrasonic chamber, a laser source for supplying a laser beam to the sample cell, and sensor detector system for detecting the scattering of the laser beam by particles in the sample cell.

As a result of the present invention, the diluent is sprayed into the sample cup to completely wash the sample particulates out of the sample cup, whereby the entire quantity of the sample within the sample cup is supplied to the ultrasonic chamber.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the generic principles of the present invention have been defined herein specifically to provide an improved sample container discharge system for a particle-size distribution analyzer.

Figure 1:
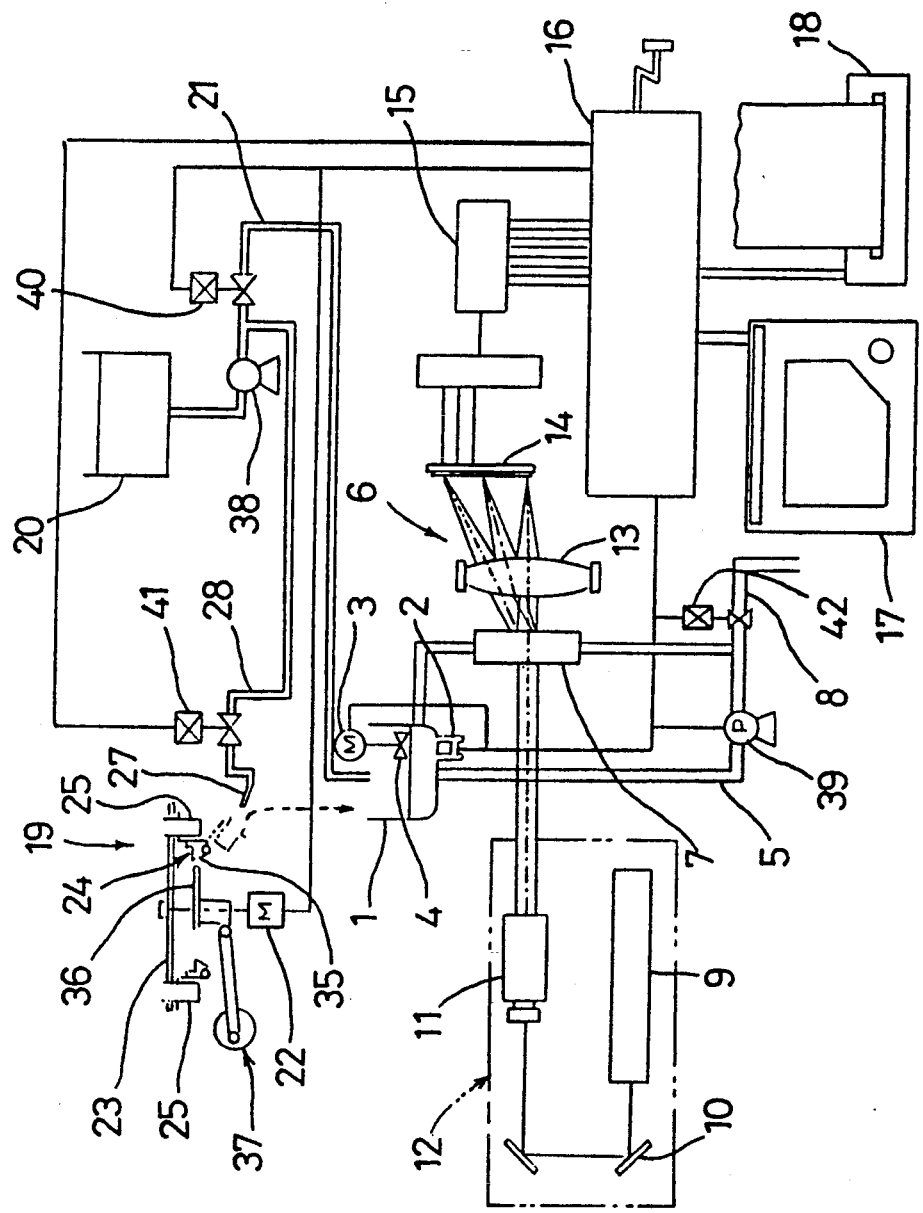
FIG. 1 is a drawing showing a schematic of a laser scattering particle-size distribution analyzer of the present invention.

The preferred embodiment of the present invention will be below described with reference to the drawings. FIG. 1 schematically shows a laser scattering particle-size distribution analyzer. An ultrasonic chamber 1 is provided with an ultrasonic vibrator 2 in a bottom portion thereof and a stirring blade 4, driven by a motor 3 therewithin. The ultrasonic chamber ensures a proper mixing of a sample with a diluent before measurement. A sample-circulating pipe 5 connects the ultrasonic chamber with a sample cell 7 at a measuring station 6. A drain pipe 8 is connected with the sample-circulating pipe 5.

The measuring station 6 comprises a laser source 12 consisting of a laser transmitter 9, a mirror 10, and a beam expander 11 arranged on one side of the sample cell 7 and a collecting lens 13 and a sensor detector 14 arranged on the other side of the sample cell 7. Particles contained within the sample cell scatter the laser light which is detected by the sensor 14.

A detected signal from the detector 14 is sent to a CPU 16 through an A/D convertor 15 to display the state of particle-size distribution of the sample to a CRT 17 and to print out the displayed result by means of a printer 18.

A sample-supplying device 19 supplies the ultrasonic chamber 1 with a sample at a discharge station. Reference numeral 20 designates a dilution unit for making a concentration of the sample within the chamber 1 to a predetermined constant value and a supply pipe 21 supplies a diluent from the dilution unit 20 to the ultrasonic chamber 1.

Figure 2:
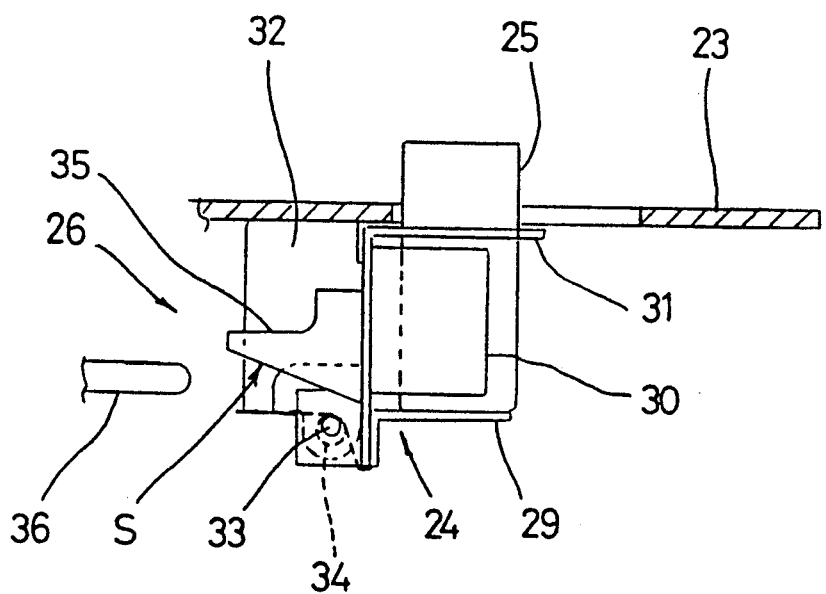
FIG. 2 is a particle cross-sectional view showing a sample cup holder arrangement.
Figure 3:
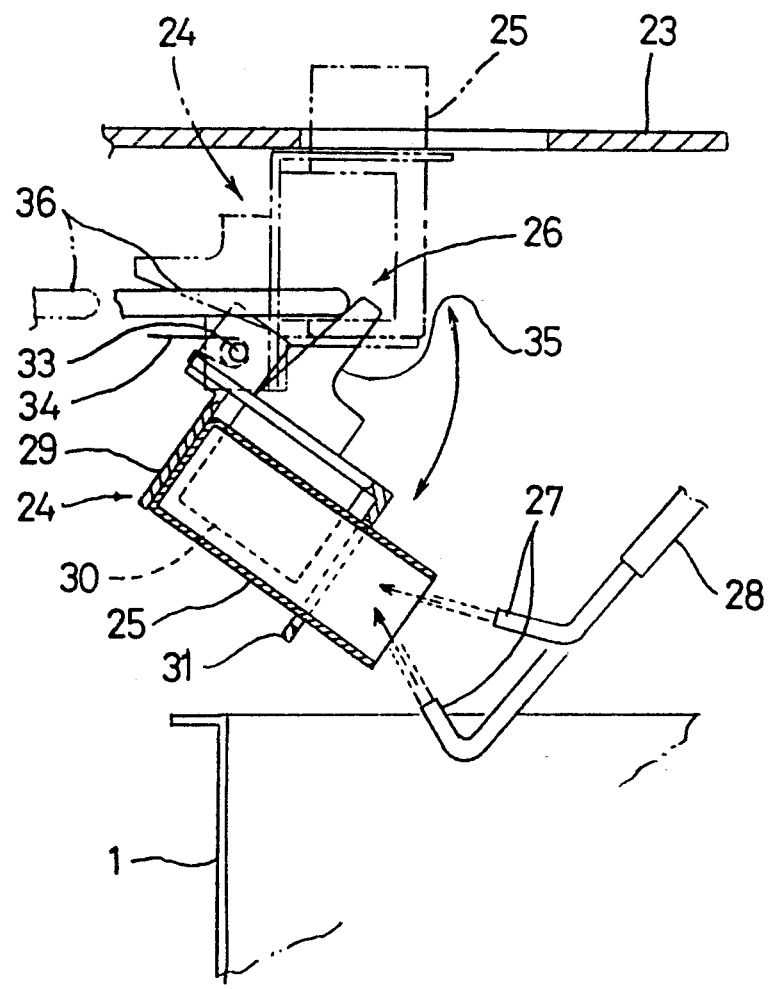
FIG. 3 is a partial cross-sectional view showing a sample cup inverted at a discharge station.

A part of the sample-supplying device 19, as shown also in FIGS. 2, 3, comprises a rotary table 23 driven by a motor 22, a plurality of cup holders arranged at appointed intervals on a circumferential portion of the rotary table 23, a holder inverting mechanism 26 for turning the sample cups 25 held by the cup holders 24 reversely up and down together with the cup holders 24 at a position above the ultrasonic bath 1. Two nozzles 27 for spraying diluent into the inverted sample cups 25. The nozzles 27 are connected with a pipe 28 branched from the diluent-supplying pipe 21.

The cup holder 24 comprises a support plate 29 for receiving a bottom portion of the sample cup 25, a holder 30 of a flat spring structure for elastically engaging a trunk portion of the cup 25 supported by the support plate 29 and an engaging member 31 for the sample cup 25. The cup holder 24 is pivoted on a bracket 32 connected downwardly from a lower surface of the rotary table 23 so as to be rotatable around a horizontal axis 33. A pivoting portion of the horizontal axis 33 is provided with a spiral spring 34 for energizedly holding or biasing the support plate 29 to an upright horizontal position.

The holder inverting mechanism 26 has the following construction. As shown in FIGS. 1 to 3, a cam member 35, of which the lower surface side is formed into the form of a cam surface S, is connected with the cup holder 24. A push rod 36 can press the cam surface S against the force of spring 34 to turn the cup holder 24 reversely upside down. The push rod is positioned to move in the radial direction from the side of a center of rotation of the rotary table 23, and a crank mechanism 37 is connected with the push rod 36 to drive it.

Figure 4:
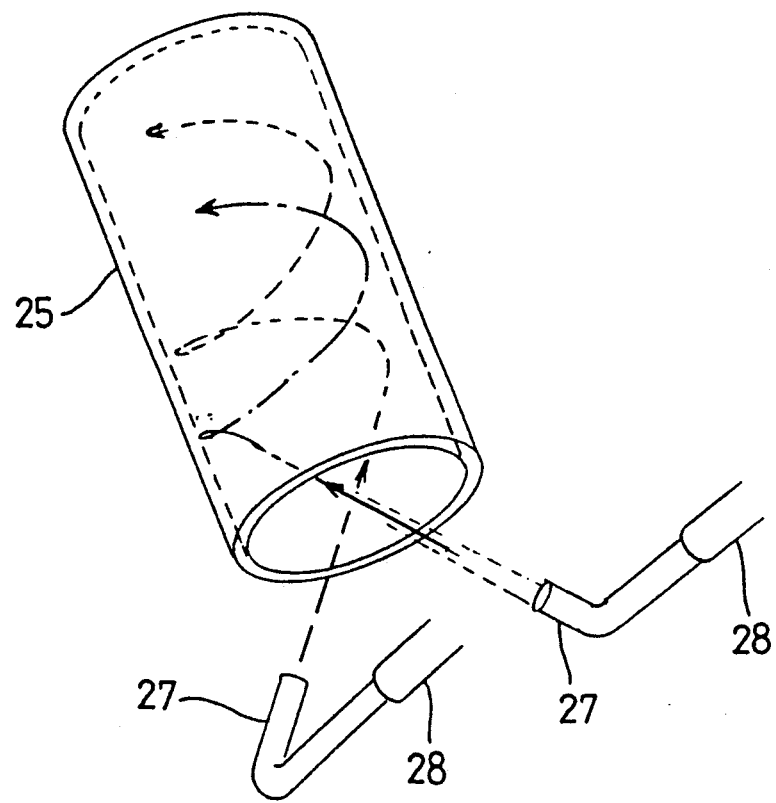
FIG. 4 is a perspective view showing a diluent sprayed into the sample cup by means of a nozzle.
Figure 5:
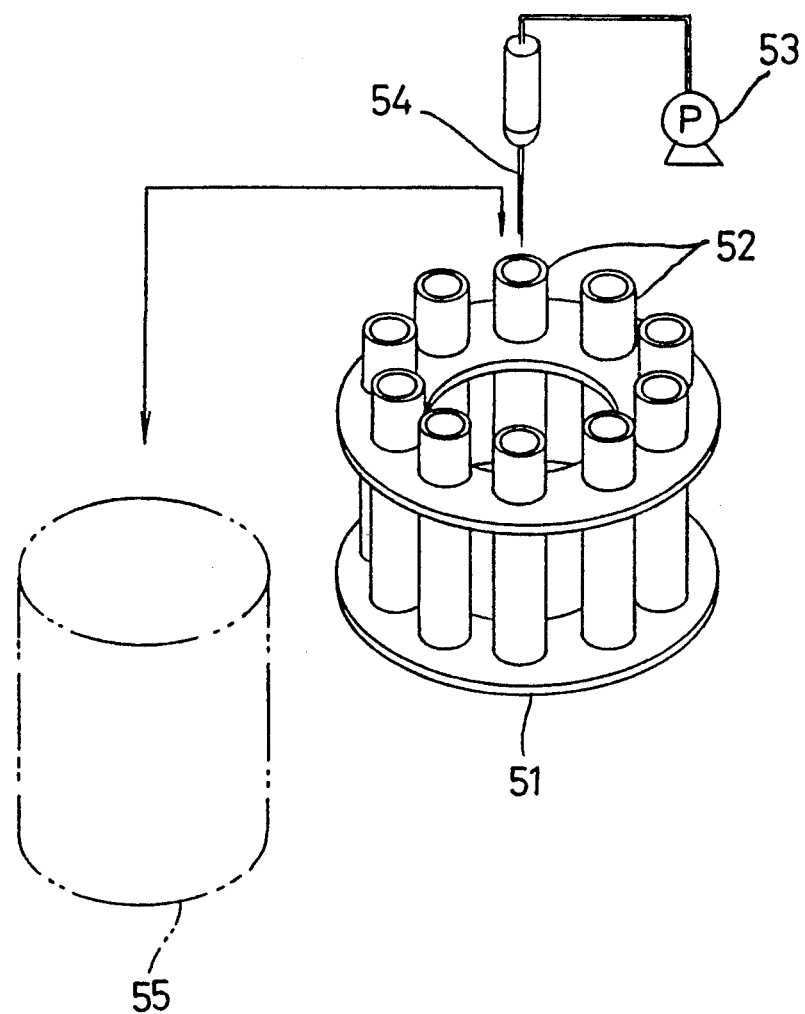
FIG. 5 is a schematic perspective view showing a conventional sample-supplying device.

In addition, as shown in FIG. 4, two nozzles 27 are arranged at symmetrical positions relatively to a center of the cup 25 with respective spraying directions of the diluent different from each other under a condition that spraying ports of the diluent will face an opening of the sample cup 25 when turned reversely upside down so that the sprayed diluent may be revolved or swirled within the cup 25 to wash the sample particulates out of the cup 25, including the bottom surface, whereby supplying the ultrasonic chamber 1 with the complete sample.

According to the above described construction, as soon as the cup 25 with the appointed sample housed therein arrives at the discharge position above the ultrasonic chamber 1, the crank mechanism 37 is operated to turn the sample cup 25 reversely upside down integrally with the cup holder 24, whereby the sample within the sample cup 25 is gravity supplied into the ultrasonic chamber 1.

The diluent is sprayed into the sample cup 25 from two nozzles 27 through the cup opening turned downwards by the above described inversion to wash out the sample within the cup 25 and flush the sample into the ultrasonic chamber 1, whereby the whole quantity of the sample within the sample cup 25 is supplied to the ultrasonic chamber 1.

In addition, referring to FIG. 1, reference numeral 38 designates a pump for sending a diluent under pressure, reference numeral 39 designates a sample-circulating pump, reference numeral 40 designates an electro-magnetic valve for controlling the quantity of diluent supplied, reference numeral 41 designates an electro-magnetic valve for branchedly supplying the nozzles 27 with a part of the diluent of which the quantity supplied has been controlled, and reference numeral 42 designates a drain valve provided in the drain pipe 8. These members 38 to 42, the ultrasonic vibrator 2 and the motors 3, 22, are controlled by programmed instructions from the CPU 16, respectively.

As above described, with the sample-supplying device according to the present invention a reduced-space sample supply mode, in which the sample cups are automatically inverted and washed free of particulates, is adopted, so that the apparatus can be small sized. The diluent that is normally mixed only in the ultrasonic chamber can be advantageously used to flush the sample container free of the sample liquid.

Thus the diluent required for making a predetermined concentration of the sample is effectively utilized, that is, the sample within the sample cup is washed out with a part of the liquid used as the diluent to be supplied in the ultrasonic chamber so that the whole quantity of the sample within the sample cup can be supplied to the ultrasonic chamber and thus the whole quantity of the sample becomes an object to be measured, whereby reproducibility can be improved and a stabilized measurement can be achieved with high accuracy, even though a sample can have a large specific gravity and a high viscosity, which can settle the components to be measured at the bottom of a sample container.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. In a laser scattering particle-size distribution analyzer having means for supplying a sample to a sample cell, the improvement comprising;
    at least one sample cup;
    a support member for movably supporting the sample cup;
    a sample cup holer pivotally mounted on the support member with a cam surface;
    means for inverting the sample cup to discharge the sample to introduce it to the supplying means, including a push rod for contacting the cam surface; and
    means for spraying the inverted sample cup to ensure a full discharge of the sample.

2. The analyzer of claim 1 wherein the means for spraying includes a pair of nozzles positioned to swirl a diluent fluid inside the sample cup.

3. The analyzer of claim 1 further including a spring member biasing the sample cup holder to an upright position.

4. The analyzer of claim 3 wherein the support member is a rotatable table and a plurality of sample cups and sample cup holders are pivotally mounted on the rotatable table.

5. The analyzer of claim 1 wherein the cup holders include a spring member for fixedly holding the sample cup in the sample cup holder.

6. The sample discharge apparatus of claim 1 wherein the spraying means includes a pair of nozzles positioned to swirl a diluent fluid inside the sample container.

7. An improved laser scattering particle-size distribution analyzer comprising;
    a plurality of sample cups;

a rotary table for movably mounting the plurality of sample cups;

means for inverting a sample cup to discharge the sample contained therein at a discharge station;

a source of diluent fluid;

means for spraying the diluent fluid into a bottom of the inverted sample cup at the discharge station to ensure a complete discharge of the sample;

ultrasonic means for receiving the discharged sample to mix it;

a sample cell fluidly connected to the ultrasonic means;

laser means for supplying a laser beam to the sample cell, and sensor means for detecting the scattering of the laser beam by particles in the sample cell.

8. The analyzer of claim 7 wherein the means for spraying includes a pair of nozzles positioned to swirl a diluent fluid inside the sample cup.

9. The analyzer of claim 8 further including a sample cup holder pivotally mounted on a support member with a cam surface and the means for inverting includes a push rod for contacting the cam surface.

10. The analyzer of claim 9 further including a spring member biasing the sample cup holder to an upright position.

11. The analyzer of claim 10 wherein the cup holders include a second spring member for fixedly holding the sample cup in the sample cup holder.

12. A sample discharging apparatus for ensuring the complete discharge of a particle containing fluid that can settle in a bottom of a sample container comprising;

a holder member for the sample container;

means for inverting the sample container mounted in the holder member at a discharge station; and spraying means positioned at the discharge station to spray the bottom of the sample container to ensure a complete discharge including a pair of nozzles positioned to swirl a diluent fluid inside the sample container.

13. The sample discharging apparatus of claim 12 further including a rotatable table and a plurality of sample containers and holder members are pivotally mounted on the rotatable table.

14. The sample discharge apparatus of claim 13 further including a cam surface on each holder member and the means for inverting includes a push rod for contacting the cam surface.

15. The sample discharge apparatus of claim 14 further including a spring member biasing the holder member to an upright position.

16. The sample discharge apparatus of claim 12 wherein each holder member includes a spring member for fixedly holding the sample container in the holder member.

17. In a laser scattering particle-size distribution analyzer having means for supplying a sample to a sample cell, the improvement comprising;

at least one sample cup;

a support member for movably supporting the sample cup;

means for inverting the sample cup to discharge the sample to introduce it to the supplying means, and means for spraying the inverted sample cup to ensure a full discharge of the sample including a pair of nozzles positioned to swirl a diluent fluid inside the sample cup.

* * * * *